United States Patent [19]

Uno et al.

[11] Patent Number: 5,723,655

[45] Date of Patent: Mar. 3, 1998

[54] AMINE COMPOUND AND DETERGENT COMPOSITION CONTAINING THE SAME

[75] Inventors: Mitsuru Uno; Tomohito Kitsuki, both of Wakayama; Katsumi Kita, Izumisano, all of Japan

[73] Assignee: Kao Corporation, Tokyo, Japan

[21] Appl. No.: 750,981

[22] PCT Filed: May 23, 1995

[86] PCT No.: PCT/JP95/00988

§ 371 Date: Jan. 7, 1996

§ 102(e) Date: Jan. 7, 1996

[87] PCT Pub. No.: WO96/01805

PCT Pub. Date: Jan. 25, 1996

[30] Foreign Application Priority Data

Jul. 8, 1994 [JP] Japan ..................... 6-157553
Jul. 8, 1994 [JP] Japan ..................... 6-157554

[51] Int. Cl.⁶ ............... C07C 229/26; C07C 229/30; C07C 233/36; C07C 235/10

[52] U.S. Cl. ............ 562/58; 510/123; 510/124; 510/125; 510/130; 510/220; 510/223; 510/226; 510/228; 510/235; 510/237; 510/300; 510/321; 510/322; 510/323; 560/180; 560/195; 560/196; 560/251; 562/36; 562/556; 562/561; 562/564; 562/565

[58] Field of Search ............ 560/180, 195, 560/196, 251; 562/36, 58, 556, 561, 564, 565; 564/154, 159; 510/123, 124, 125, 130, 220, 223, 226, 228, 235, 237, 300, 321, 322, 323

[56] References Cited

FOREIGN PATENT DOCUMENTS 58-92650  6/1983  Japan.

*Primary Examiner*—Peter O'Sullivan
*Attorney, Agent, or Firm*—Oblon, Spivak, McClelland, Maier & Neustadt, P.C.

[57] ABSTRACT

The present invention relates to an amine compound represented by the following general formula (1):

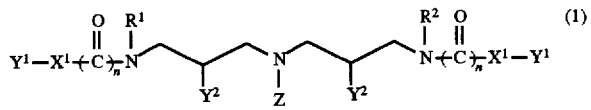

wherein $R^1$ and $R^2$ represent individually a linear or branched $C_1$–$C_{24}$ alkyl or alkenyl group which may be substituted by a hydroxyl group, $X^1$ represents a $C_1$–$C_6$ alkylene or alkenylene group which may be substituted by a hydroxyl, sulfonic or carboxyl group, $Y^1$ represents a carboxyl or sulfonic group, or a sulfuric acid residue, $Y^2$ represents a hydroxyl group, a sulfuric acid residue or a group —OCO—$X^1$—COOH, Z represents a sulfoalkyl group or a group obtained by removing an amino group from an amino acid or a salt thereof, and n represents a number of 0 or 1, or a salt or quaternized product thereof, an intermediate useful for the preparation thereof, and detergent compositions containing such an amine compound. This compound is low in irritativeness to the skin and hair and excellent in foamability, and can give a pleasant feeling to the user's skin and the like.

6 Claims, No Drawings

AMINE COMPOUND AND DETERGENT COMPOSITION CONTAINING THE SAME

This application is a 371 of PCT/JP95/00988 filed 23 May 1995.

TECHNICAL FIELD

The present invention relates to a novel amine compound, which is useful as a base for hair and skin cosmetic compositions, a detergent, an emulsifying agent, a conditioning agent, or the like, an intermediate useful for the preparation thereof, and detergent compositions containing such an amine compound.

BACKGROUND ART

Surfactants such as alkylsulfates, polyoxyethylene alkylsulfates and alkylbenzenesulfonates have heretofore been used as detergents. However, many of these surfactants involve a problem that they irritate the skin to a somewhat strong extent upon their use. For this reason, surfactants low in skin irritation, such as alkylphosphates and salts of acylated amino acids, have come to be used as bases or emulsifying agents for hair and skin cosmetic compositions, or detergents for the skin and the like. With the diversification of consumer demand and inclination to high-quality goods, there have recently been demand for development of compounds which have good foamability and such effects that a pleasant feeling can be given to the user's skin and the like, in addition to low irritativeness to the skin and the like. However, no compound fully satisfying these requirements has been yet developed.

Accordingly, it is an object of the present invention to provide a compound which can solve the above problems, has low irritativeness to the skin and the like and excellent foamability, can give a pleasant feeling to the user's skin and the like, and is useful as a base for hair and skin cosmetic compositions, a detergent, an emulsifying agent, a conditioning agent, and the like.

In view of the foregoing circumstances, the present inventors have carried out an extensive investigation. As a result, it has been found that novel amine compounds represented by the general formula (1), which will be described subsequently, can serve as anionic surfactants, have low irritativeness to the skin and the like, give a pleasant feeling to the user's skin and the like, and have excellent foamability, thus leading to completion of the present invention.

Incidentally, as compounds having a structure close to that of the compounds according to the present invention, there have been known compounds having a 2-hydroxypropanediamine structure (U.S. Pat. No. 3,654,158, DE Patent No. 3,607,884, U.S. Pat. No. 4,982,000 and Japanese Patent Application Laid-Open Nos. 233264/1989 and 223515/1990, etc.). Since these compounds have a diamine structure and besides have no anionic functional groups such as a carboxyl group, a sulfonic group and a sulfuric acid residue, however, they are greatly different from the compounds of the present invention, which are anionic surfactants having a triamine structure, in both structure and function.

DISCLOSURE OF THE INVENTION

According to the present invention, there is thus provided an amine compound represented by the following general formula (1):

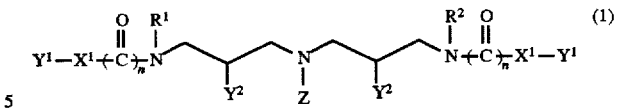

wherein $R^1$ and $R^2$ are the same or different from each other and represent individually a linear or branched alkyl or alkenyl group which may be substituted by a hydroxyl group and has 1–24 carbon atoms, $X^1$ represents an alkylene or alkenylene group which may be substituted by at least one hydroxyl, sulfonic or carboxyl group and has 1–6 carbon atoms, $Y^1$ represents a carboxyl or sulfonic group, or a sulfuric acid residue, $Y^2$ represents a hydroxyl group, a sulfuric acid residue or a group —OCO—$X^1$—COOH, Z represents a sulfoalkyl group or a group obtained by removing an amino group from an amino acid or a salt thereof, and n represents a number of 0 or 1, or a salt or quaternized product thereof.

According to the present invention, there is also provided an aminoalcohol compound which is an intermediate useful for the preparation of the amine compound (1) and represented by the following general formula (2):

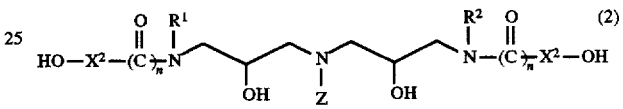

wherein $R^1$ and $R^2$ are the same or different from each other and represent individually a linear or branched alkyl or alkenyl group which may be substituted by a hydroxyl group and has 1–24 carbon atoms, $X^2$ represents an alkylene or alkenylene group which may be substituted by at least one hydroxyl group and has 1–6 carbon atoms, Z represents a sulfoalkyl group or a group obtained by removing an amino group from an amino acid or a salt thereof, and n represents a number of 0 or 1.

According to the present invention, there is further provided a detergent composition comprising the amine compound represented by the general formula (1), or a salt or quaternized product thereof.

BEST MODE FOR CARRYING OUT THE INVENTION

In the general formulae (1) and (2), the linear or branched alkyl or alkenyl groups represented by $R^1$ and $R^2$, which may be substituted by a hydroxyl group and have 1–24 carbon atoms, are preferably linear or branched alkyl or alkenyl groups which may be substituted by a hydroxyl group and have 6–24 carbon atoms, more preferably linear or branched alkyl or alkenyl groups having 6–24 carbon atoms, still more preferably linear or branched alkyl groups having 6–12 carbon atoms, and particularly preferably linear alkyl groups having 6–10 carbon atoms.

As the linear alkyl groups, may be mentioned methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. Examples of the branched alkyl groups may include groups such as methylhexyl, ethylhexyl, methylheptyl, ethylheptyl, methylnonyl, methylundecyl, methylheptadecyl, hexyldecyl and octyldecyl.

As examples of the linear alkenyl groups, may be mentioned groups such as ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl and tetracosenyl. As examples of the branched alkenyl groups, may be mentioned groups such as methylhexenyl, ethylhexenyl, methylheptenyl, ethylheptenyl, methylnonenyl, methylundecenyl, methylheptadecenyl, hexyldecenyl and octyldecenyl.

With respect to the linear or branched alkyl or alkenyl groups substituted by a hydroxyl group, no particular limitation is imposed on the position substituted by the hydroxyl group. Examples thereof include groups in which a hydroxyl group has been substituted at an optional position of the above-mentioned alkyl or alkenyl groups.

In the general formula (1), the linear or branched alkylene or alkenylene group represented by $X^1$, which may be substituted by at least one hydroxyl, carboxyl or sulfonic group and has 1–6 carbon atoms, is preferably a group having 1–4 carbon atoms, more preferably a group having 1–3 carbon atoms. Examples of the alkylene or alkenylene group having 1–6 carbon atoms include methylene, ethylene, trimethylene, tetramethylene, pentamethylene, hexamethylene, methylethylene, ethylethylene, ethenylene, propenylene, butenylene, pentenylene and hexenylene groups. Of these, methylene, ethylene, trimethylene and ethenylene groups are particularly preferred.

These alkylene or alkenylene groups may be substituted by at least one hydroxyl group, sulfonic group (—$SO_3H$) or carboxyl group (—COOH). These substituent groups may be substituted either singly or in any combination of 2 to 4 groups of the same kind or different kinds. Preferable examples of the hydroxyl-substituted alkylene or alkenylene groups include 1,2-dihydroxyethylene, 1-hydroxytrimethylene and 2-hydroxytrimethylene groups. Preferable examples of the sulfonic group-substituted alkylene or alkenylene groups include 1-sulfoethylene and 2-sulfoethylene groups. Particularly preferable examples of the carboxyl group-substituted alkylene or alkenylene groups include 1-carboxyethylene and 2-carboxyethylene groups.

As the alkylene or alkenylene group substituted by hydroxyl and carboxyl groups, 2-carboxy-2-hydroxytrimethylene group is particularly preferred. As the alkylene or alkenylene group substituted by hydroxyl and sulfonic groups, 1-hydroxy-2-sulfoethylene and 2-hydroxy-1-sulfoethylene groups are particularly preferred.

Examples of the linear or branched alkylene or alkenylene group represented by $X^2$ in the general formula (2), which may be substituted by at least one hydroxyl group and has 1–6 carbon atoms, include those exemplified as $X^1$.

in the general formulae (1) and (2), Z represents a sulfoalkyl group or a group obtained by removing an amino group from an amino acid or a salt thereof. As specific examples of this amino acid, may be mentioned asparagin, aspartic acid, alanine, arginine, isoleucine, glycine, glutamine, glutamic acid, cystine, cysteine, serine, tyrosine, tryptophan, threonine, valine, histidine, hydroxyproline, hydroxylysine, phenylalanine, proline, methionine, lysine, leucine, β-alanine, α-aminobutyric acid, isoserine, ornithine, glutathione, glycylglycine, γ-aminocapronic acid and citrulline. Of these, as Z, sulfo-$C_1$–$C_6$-alkyl groups and groups obtained by removing an amino group from a protein-constituting amino acid, β-alanine or a salt thereof are preferred, with a sulfoethyl group being particularly preferred.

Since the compounds (1) according to the present invention have at least one sulfonic group (—$SO_3H$), sulfuric acid residue (—$OSO_3H$) or carboxyl group (—COOH), they can form salts with various basic substances. Examples of such salts may include alkali metal salts, alkaline earth metal salts, amine salts, basic amino acid salts and ammonium salts. As specific examples of the salts, may be mentioned salts with sodium, potassium, lithium, magnesium, calcium, trimethylamine, triethylamine, tributylamine, monoethanolamine, diethanolamine, triethanolamine, lysine, arginine, choline and ammonia. Of these, the sodium, potassium and ammonium salts are preferred.

Incidentally, since the compounds (1) according to the present invention have tertiary amino groups, they may have a quaternary salt structure that a proton is coordinated on the nitrogen atom of the tertiary amino group, and so the tertiary amino group turns into an ammonium cation, and the sulfonic group or carboxyl group becomes a sulfonate or carboxylate anion.

The compounds (1) according to the present invention may be quaternized as needed. Specific examples thereof include compounds in which all or part of the three nitrogen atoms have been quaternized if n in the formula (1) is 0. As examples of the group capable of bonding to the nitrogen atom for the quaternization, may be mentioned alkyl groups which may be substituted by at least one hydroxyl, carboxyl or sulfonic group and have 1–6 carbon atoms, a benzyl group, and groups represented by —($R^3O$)$_m$H in which $R^3$ represents an alkylene group having 2–4 carbon atoms, and m represents a number of 1–50. Here, examples of the alkyl groups which may be substituted by at least one hydroxyl, carboxyl or sulfonic group and have 1–6 carbon atoms include methyl, ethyl, propyl, isopropyl, butyl, pentyl, hexyl, hydroxyethyl, 1,2-dihydroxypropyl, carboxymethyl and 2-hydroxy-3-sulfopropyl groups. Specific examples of the groups represented by the radical —($R^3O$)$_m$H include polyoxyethylene and polyoxypropylene groups. Of these groups, those in which m is 1–20 are preferred.

The amine compounds (1) according to the present invention can be prepared in accordance with, for example, the following reaction schemes a to d:

[Reaction Scheme a (case of n = 0 in the formula (1))]

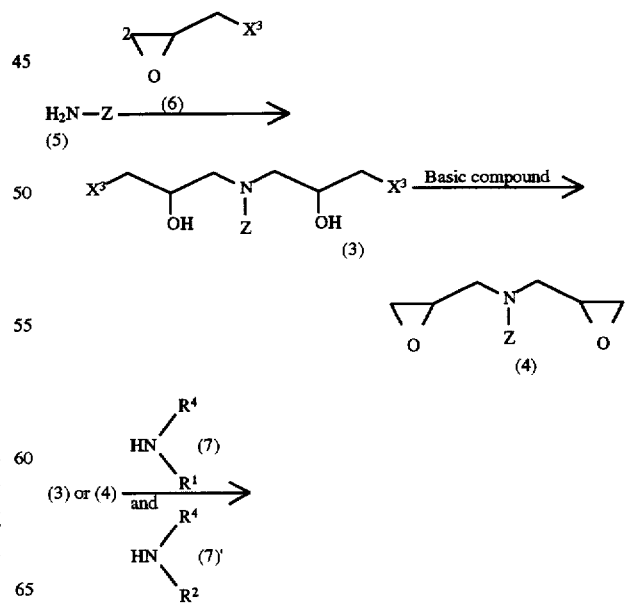

-continued
[Reaction Scheme a (case of n = 0 in the formula (1))]

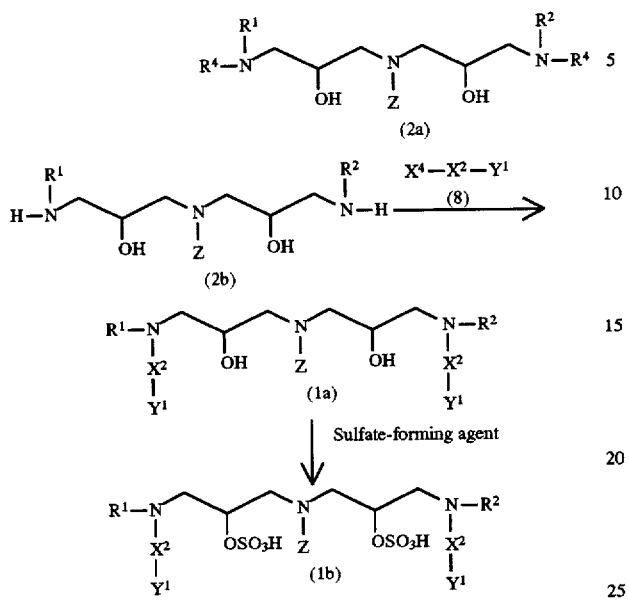

wherein $R^1$, $R^2$, $X^2$, $Y^1$ and Z have the same meaning as defined above, $X^3$ and $X^4$ represent individually a halogen atom, and radicals $R^4$ are the same or different from each other and represent individually a hydrogen atom or a linear or branched alkyl or alkenyl group which may be substituted by a hydroxyl group and has 1–24 carbon atoms.

More specifically, an aminoalkylsulfonic acid, an amino acid or a salt thereof (5) is reacted with an epihalohydrin (6), thereby obtaining a novel halohydrin compound (3). This halohydrin compound (3) or a novel epoxy compound (4) obtained by reacting the compound (3) with a basic compound is reacted with amine compounds (7) and (7)', thereby obtaining a novel amine compound (2a). An amine compound (2b) in which $R^4$ in the amine compound (2a) is a hydroxyl group is reacted with a compound (8), thereby obtaining an amine compound (1a) according to the present invention. Further, the amine compound (1a) is reacted with a sulfating agent, thereby obtaining a compound (1b).

Examples of the halogen atom in the epihalohydrin (6) used in the synthesis of the halohydrin compound (3), i.e., $X^3$ in the formula (6), include chlorine, bromine and iodine, with chlorine being preferred. The reaction of the aminoalkylsulfonic acid, amino acid or salt thereof (5) with the epihalohydrin (6) may be conducted, for example, at a temperature of preferably −20° to 100° C., particularly preferably 0° to 60° C. in a solvent inert to the reaction, such as water, a lower alcohol or a mixture of these solvents. The proportion of the compound (5) and epihalohydrin (6) to be used may be suitably preset. However, it is preferable to use the epihalohydrin (6) in an amount of 2–5 moles per mole of the compound (5).

The halohydrin compound (3) thus obtained can be reacted with the basic compound into the epoxy compound (4). Preferable examples of the basic compound used in such a reaction include alkali metal hydroxides, alkali metal carbonates and amines, with sodium hydroxide and potassium hydroxide being particularly preferred. The reaction of the halohydrin compound (3) with the basic compound may be conducted, for example, at preferably 0°–80° C., particularly preferably 20°–60° C. in a solvent inert to the reaction, such as water, a lower alcohol or a mixture of these solvents.

The proportion of the halohydrin compound (3) and basic compound to be used may be suitably preset. However, it is preferable to use the basic compound in an amount of 2–5 moles per mole of the halohydrin compound (3).

The subsequent reaction of the thus-obtained halohydrin compound (3) or epoxy compound (4) with the amine compounds (7) and (7)' may be conducted, for example, at preferably 40°–150° C., particularly preferably 70°–120° C. in a solvent inert to the reaction, such as water, a lower alcohol, an ether, an aromatic hydrocarbon or a mixture of these solvents. The proportion of the respective compounds to be used in the reaction may be suitably preset. However, it is generally preferable to use the amine compounds (7) and (7)' in an amount of 2–20 moles, particularly 2–10 moles per mole of the halohydrin compound (3) or the epoxy compound (4).

Among the amine compounds (2a) obtained in this manner, an amine compound (2b) in which $R^4$ is a hydrogen atom is reacted with the compound (8) or a salt thereof, thereby obtaining the amine compound (1a) according to the present invention. In the case where the salt of the compound (8) is used in this reaction, examples of such a salt include alkali metal salts and amine salts, specifically, the sodium, potassium and ammonium salts. The reaction of the amine compound (2b) with the compound (8) or the salt thereof may be conducted, for example, at preferably 40°–150° C., particularly preferably 70°–100° C. in a solvent inert to the reaction, such as water, a lower alcohol or a mixture of these solvents while maintaining the pH of the reaction system at 8–10. The proportion of the amine compound (2b) and the compound (8) or the salt thereof to be used may be suitably preset. However, it is generally preferable to use the amine compound (2b) in an amount of 2–20 moles, particularly 2–10 moles per mole of the compound (8) or the salt thereof.

In the above-described manner, the amine compound (1a) according to the present invention can be obtained. In addition to the intended compound, however, there may be secondarily formed or left salts of an amine and an acid, inorganic salts, respective unreacted compounds or salts thereof, by-products formed by the reaction at only one of two reaction sites present in each reaction, for example, a compound represented by the following formula:

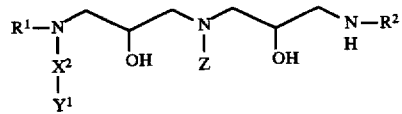

and the like according to the reaction conditions. This reaction product may be used for various purposes as it is. If a higher-purity product is required, however, it may be purified by a method known per se in the art, such as solvent fractionation, dialysis, recrystallization, distillation, partition chromatography or gel filtration. Although the intended product thus obtained may be isolated as a free base, it may be subjected to salt interchange by a usual means such as neutralization with a desired basic substance, thereby isolating it in the form of the desired salt. Examples of such a basic substance include sodium hydroxide, potassium hydroxide, lithium hydroxide, magnesium hydroxide, calcium hydroxide, ammonia, trimethylamine, triethylamine, tributylamine, alkanolamines (monoethanolamine, diethanolamine, triethanolamine, etc.), lysine, arginine and choline. Of these, the alkali metal hydroxides such as sodium hydroxide and potassium hydroxide may preferably be used.

The reaction of the thus-obtained aminoalcohol (1a) with the sulfate-forming agent is preferably conducted in a temperature range of from −75° C. to 150° C. in an inert solvent or without any solvent. As the sulfate-forming agent, ClSO$_3$H, SO$_3$ or the like is used, and its amount to be used is preferably controlled to 1–10 moles, particularly 2–5 moles per mole of the aminoalcohol (1a). Neutralization which is optionally conducted after completion of this reaction is performed by causing a basic substance such as sodium hydroxide, potassium hydroxide, lithium hydroxide, magnesium hydroxide, calcium hydroxide, ammonia, trimethylamine, triethylamine, tributylamine, alkanolamine (monoethanolamine, diethanolamine, triethanolamine or the like), lysine, arginine or choline, preferably, an alkali metal hydroxide such as sodium hydroxide or potassium hydroxide to react in a desired amount according to the intended neutralization degree.

[Reaction Scheme b (case of n = 1 in the formula (1))]

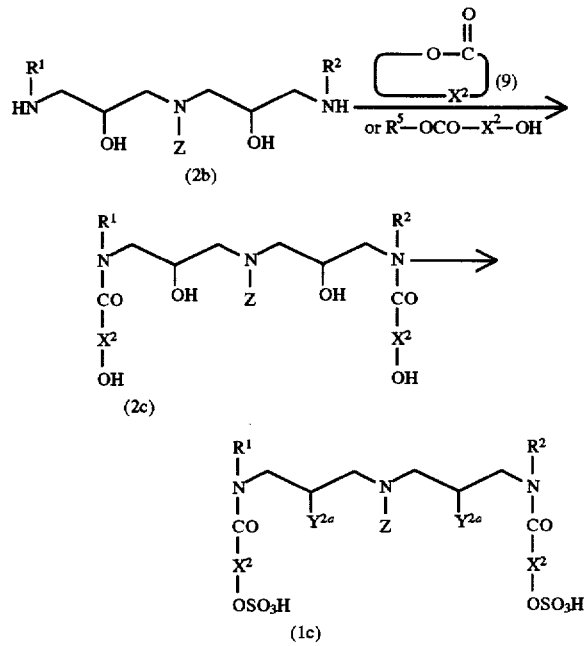

(2b)

(2c)

(1c)

wherein R$^1$, R$^2$, X$^2$ and Z have the same meaning as defined above, and R$^5$ represents a hydrogen atom or a linear or branched alkyl group having 1–4 carbon atoms, and Y$^2$a represents a hydroxyl group or a sulfuric acid residue.

More specifically, the amine derivative (2b) is reacted with a lactone (9) or a hydroxycarboxylic acid (10). The resultant aminoalcohol (2c) is then reacted with a sulfate-forming agent, and the reaction product is optionally neutralized with a basic substance, thereby preparing a compound (1c) according to the present invention or a salt thereof.

The reaction of the amine derivative (2b) with the lactone (9) or the hydroxycarboxylic acid (10) is preferably conducted, for example, by reacting the amine derivative (2b) with the lactone (9) or the hydroxycarboxylic acid (10) in an amount of 2–5 moles per mole of the amine derivative (2b) at preferably 20°–180° C., particularly preferably 40°–150° C. in an inert solvent or without any solvent. No particular limitation is imposed on the inert solvent used in this reaction so far as it is an aprotic solvent. However, lower hydrocarbons, aromatic hydrocarbons, ethers, halogenated hydrocarbons and the like are preferred in view of price and solubility. With respect to the lactone (9) and the hydroxycarboxylic acid (10) used in this reaction, γ-lactone, δ-lactone, etc. as the lactone (9) and glycolic acid, lactic acid, α-hydroxy acid, the methyl esters and ethyl esters of these acids, etc. as the hydroxycarboxylic acid (10) are preferred because they are cheap.

The reaction of the thus-obtained aminoalcohol (2c) with the sulfate-forming agent is conducted in the same manner as in the above-described reaction of the compound (1a) with the sulfate-forming agent. In the above reaction scheme, the reaction of the amine derivative (2b) and the lactone (9) or the hydroxycarboxylic acid (10) may form, as a by-product, a small amount of a compound represented by the following formula:

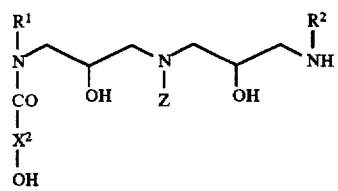

and the reaction of the aminoalcohol (2c) and the sulfate-forming agent may form, as by-products, compounds represented by the following formulae:

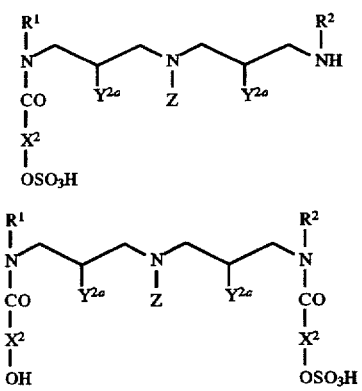

wherein R$^1$, R$^2$, Z, X$^2$ and Y$^2$a have the same meaning as defined above. This reaction product may be used for various purposes as it is. If a higher-purity product is required, however, it may be purified for use by a method known per se in the art, for example, recrystallization, column chromatography, distillation or the like.

[Reaction Scheme c (case of n = 1 in the formula (1))]

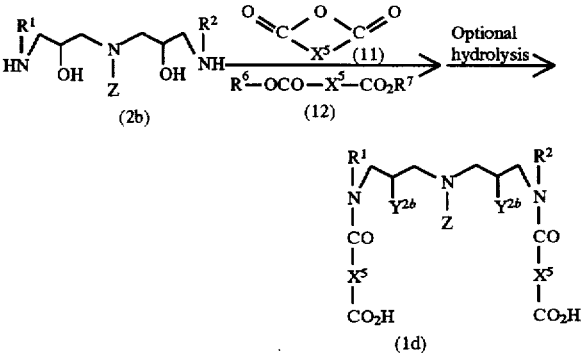

wherein R$^1$, R$^2$ and Z have the same meaning as defined above, X$^5$ represents an alkylene or alkenylene group which may be substituted by at least one hydroxyl or carboxyl group and has 2–4 carbon atoms, $R^6$ and $R^7$ are the same or different from each other and represent individually a hydrogen atom or a linear or branched alkyl or alkenyl group having 1–4 carbon atoms, and $Y^{2b}$ represents a hydroxyl group or a group —OCO—$X^5$—COOH.

[Reaction Scheme d (case of n = 1 in the formula (1))]

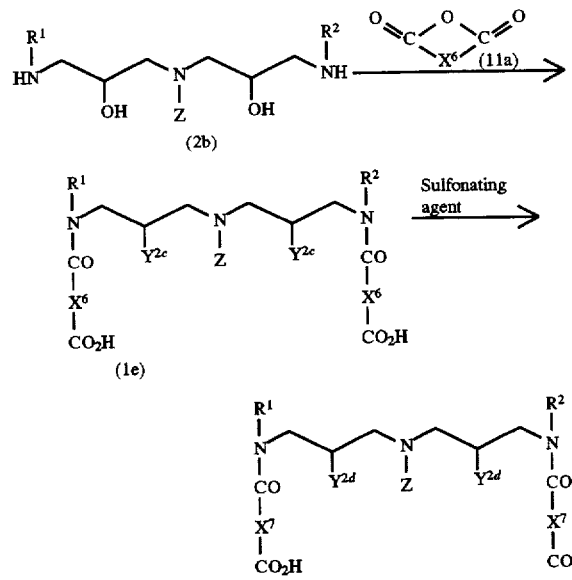

wherein $R^1$, $R^2$ and Z have the same meaning as defined above, $X^6$ represents an alkenylene group which may be substituted by at least one hydroxyl group and has 2–4 carbon atoms, $X^7$ represents an alkylene group which may be substituted by a hydroxyl group, has been substituted by a sulfonic group and has 2–4 carbon atoms, $Y^{2c}$ represents a hydroxyl group or a group —OCO—$X^6$—COOH, and $Y^{2d}$ represents a hydroxyl group or a group —OCO—$X^7$—COOH.

More specifically, the amine derivative (2b) is reacted with an acid anhydride (11), or a dicarboxylic acid or an ester thereof (12). The reaction product is hydrolyzed if the ester is used, and optionally neutralized with a basic substance, whereby an amidocarboxylic acid (1d) according to the present invention or a salt thereof can be prepared.

Among the amidocarboxylic acids (1d) according to the present invention, an amidocarboxylic acid (1e) of the present invention, in which $X^5$ is an alkenylene group ($X^6$) which may be substituted by at least one hydroxyl group and has 2–4 carbon atoms, is reacted with a sulfonating agent, and the reaction product is optionally neutralized with a basic substance, whereby an amidosulfocarboxylic acid (1f) according to the present invention or a salt thereof can be prepared.

The reaction of the amine derivative (2b) with the acid anhydride (11) or (11a) is preferably conducted, for example, by reacting the amine derivative (2b) with the acid anhydride (11) or (11a) in an amount of preferably 1.0 to 5.0 moles per mole of the amine derivative (2b) in the presence of a water-free inert solvent at 20°–150° C., preferably 40°–100° C. Examples of the water-free inert solvent used herein include ether, tetrahydrofuran, benzene and pyridine. In this reaction, a compound in which the hydroxyl groups in the amine derivative (2b) have been reacted with the acid anhydride is also formed.

Besides, the reaction of the amine derivative (2b) with the dicarboxylic acid or the ester thereof (12) is preferably conducted, for example, by reacting the amine derivative (2b) with the dicarboxylic acid or the ester thereof (12) in an amount of preferably 2.0–5.0 moles per mole of the amine derivative (2b) in the presence of an inert solvent at 40°–180° C., preferably 80°–150° C. This reaction is preferably performed while removing an alcohol or water formed. Examples of the inert solvent used in this reaction include hexane, benzene, toluene and xylene.

incidentally, as the alkyl or alkenyl groups represented by $R^6$ and $R^7$ in the formula of the dicarboxylic ester, methyl and ethyl groups are preferred.

In this reaction, an intermediate represented by the following general formula (2d) is formed when the dicarboxylic ester is used. It is hence necessary to subsequently hydrolyze the intermediate in the presence of an acid or base catalyst in, for example, a water-containing alcohol.

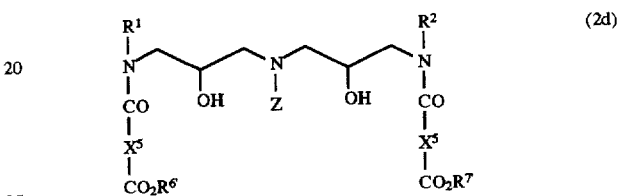

wherein $R^1$, $R^2$, $X^5$ and Z have the same meaning as defined above, and $R^{6'}$ and $R^{7'}$ represent alkyl or alkenyl groups corresponding to $R^6$ and $R^7$, respectively.

The subsequent reaction of the amidocarboxylic acid (1e) of the present invention, which has the alkenylene groups $X^6$, with the sulfonating agent is preferably conducted, for example, by reacting the compound (1e) with the sulfonating agent in an amount of 1.0–6.0 moles, preferably 2.0–5.0 moles per mole of the compound (1e) at pH 4.0–11.0, preferably 5.0–8.0 and 30°–100° C., preferably 40°–80° C. in water. As the sulfonating agent, $SO_3$, sodium sulfite or sodium hydrogensulfite is used.

The neutralization of the thus-obtained compounds (1d), (1e) and (1f) according to the present invention may be performed in the same manner as in Reaction Scheme a. In these reactions, as with the above-described Reaction Schemes b and c, compounds in which only one of the amino groups has been N-acylated, and the like are formed as by-products. However, the reaction products may be used for various purposes as they are. However, if higher-purity products are required, they may also be purified for use by a method known per se in the art, for example, recrystallization, column chromatography, electrodialysis or the like.

A compound of the general formula (1) is reacted with a quaternizing agent, whereby a compound in which all (in case of n=0) or part of the three nitrogen atoms in the compound (1) according to the present invention have been quaternized can be obtained. Examples of the quaternizing agent include alkyl halides which may be substituted by a hydroxyl, carboxyl or sulfonic group and have 1–6 carbon atoms, benzyl halides and alkylene oxides or their salts. Of these, the alkyl halides are more preferred. Examples of the alkyl group in these compounds include methyl, ethyl, n-propyl, n-butyl and isopropyl groups. Examples of the halogen include chlorine, bromine and iodine. Of these, methyl chloride is particularly preferred.

Incidentally, the compound (8) is also a quaternized agent. Therefore, when the compound (8) is reacted with the compound (1a) or (2a), their corresponding quaternized products are formed.

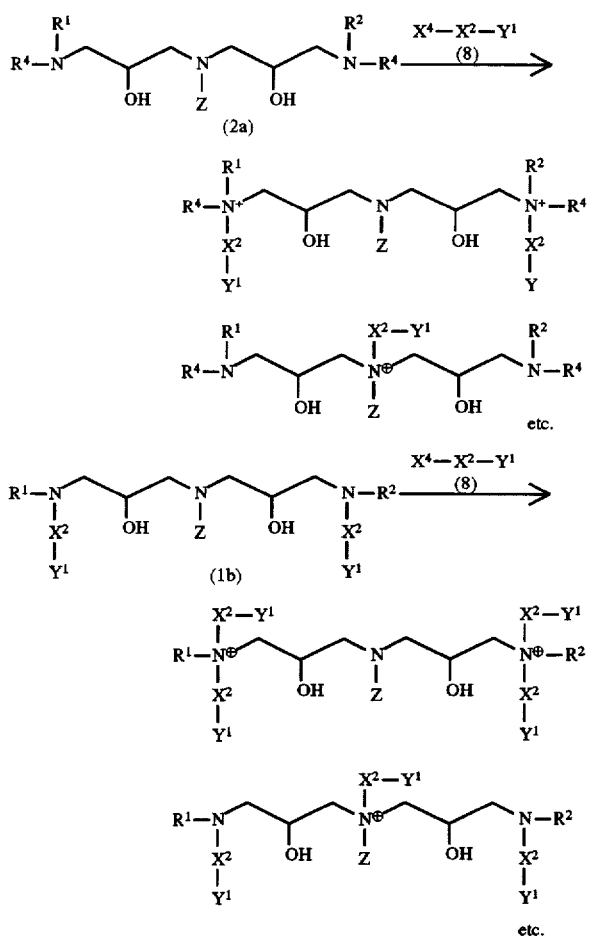

wherein $R^1$, $R^2$, $X^2$, $Y^1$, $R^4$ and Z have the same meaning as defined above.

The amine compounds of the present invention, which are represented by the general formula (1), have excellent detergency and foaming power and hence can be used in applications making good use of these properties, for example, various detergents such as skin and hair detergents, dishwashing detergents, and laundry detergents. No particular limitation is imposed on the amount of the compound (1) according to the present invention to be incorporated in that case. However, it may be used in a range of 0.1–80 wt. %, preferably 1–50 wt. % according to the intended application thereof, and the like.

Such detergent compositions may optionally contain various known surfactants, moisturizers, germicides, emulsifying agents, thickeners, pearly luster-imparting agents, divalent metal ion sequestrants, alkalifying agents, inorganic salts, resoiling preventives, enzymes, available chlorine scavengers, reducing agents, bleaching agents, fluorescent dyes, solubilizing agents, perfume bases, caking preventives, enzyme activators, antioxidants, antiseptics, coloring matter, bluing agents, bleaching activators, enzyme stabilizers, phase modifiers, penetrating agents, and the like.

As the surfactants, there may be used anionic surfactants, nonionic surfactants, amphoteric surfactants and cationic surfactants. The anionic surfactants are usually incorporated for the purpose of improving detergency, foaming power and a feel upon use. Examples thereof include higher fatty acid salts, alkylsulfates, alkyl ether sulfates, alkylsulfonates, α-olefinsulfonates, alkylbenzenesulfonates, alkanoylisethionates, alkylsuccinates, alkylsulfosuccinates, N-alkanoyl-sarcosinates, alkylphosphates, alkyl ether phosphates and alkyl ether carboxylates. The alkyl and acyl groups of these anionic surfactants generally have 8–20 carbon atoms, and may be converted to unsaturated groups. The alkyl ether sulfates, alkyl ether phosphates and alkyl ether carboxylates may contain 1–10 ethylene oxide or propylene oxide units per molecule. However, they preferably contain 2–3 ethylene oxide units per molecule. Examples of the salts of these anionic surfactants include the sodium, magnesium, ammonium and mono-, di- and triethanolamine salts.

The nonionic surfactants are usually incorporated for the purpose of improving detergency and a feeling upon use. Examples thereof include polyoxyalkylene alkyl ethers, polyoxyalkylene phenyl ethers, mono- or dialkylalkanolamides or alkylene oxide adducts thereof, alkyl polyglycosides and monoglycerides. The alkyl and acyl groups of these nonionic surfactants generally have 8–20 carbon atoms, and may be converted to unsaturated groups. The polyoxyalkylene groups thereof include polyoxyethylene, polyoxypropylene and a mixed type thereof, and their condensation degrees are generally 6–30.

Examples of the amphoteric surfactants include long-chain-alkyl-dimethylcarboxymethylbetaines and sulfobetaines. Examples of the cationic surfactants include long-chain alkyl-trimethylammonium salts and di-long-chain-alkyl-dimethylammonium salts.

These surfactants are incorporated in combination with the compound (1) according to the present invention in an amount of 0.5–60 wt. % of the detergent composition. In particular, when the detergent composition is provided in the form of powder, they are preferably incorporated in an amount of 10–45 wt. %. When the detergent composition is provided in the form of liquid, they are preferably incorporated in an amount of 20–50 wt. %. Further, when the detergent composition is provided as a bleaching detergent, the surfactants are preferably incorporated in an amount of generally 1–10 wt. %, more preferably 1–5 wt. %.

As the moisturizers, there may be used glycerol, ethylene glycol, propylene glycol, 1,3-butylene glycol and the like.

As the thickeners, there may be used polyacrylic acid, crosslinked polymers of acrylic acid, copolymers of acrylic acid and a hydrophobic monomer, copolymers of a carboxylic acid-containing monomer and an acrylic ester, crosslinked copolymers of acrylic acid and an acrylic ester, ethylene glycol ester or polyethylene glycol ester (for example, fatty acid ester thereof), and heteropolysaccharide gums.

The pearly luster-imparting agents may be selected from $C_{16-22}$ fatty acids, $C_{16-22}$ esters of a fatty acid and an alcohol, or $C_{16-22}$ fatty acid esters containing elements such as alkylene glycol units. As examples of suitable alkylene glycol units, may be mentioned ethylene glycol and propylene glycol. However, polyalkylene glycols may also be used. Examples of suitable polyalkylene glycols may include polyethylene glycol and polypropylene glycol.

As the divalent metal ion sequestrants, there may be used condensed phosphates such as tripolyphosphates, pyrophosphates and orthophosphates, aluminosilicates such as zeolite, synthetic layer lattice silicates, nitrilotriacetates, ethylenediaminetetraacetates, citrates, isocitrates, polyacetalcarboxylates and the like.

The divalent metal ion sequestrants are incorporated in an amount of 0–50 wt. %, preferably 5–40 wt. %. It is more preferable to use a divalent metal ion sequestrant containing no phosphorus.

As the alkalifying agents and inorganic salts, there are used silicates, carbonates, sesquicarbonates, sulfates, alkanolamines and the like. These components are incorporated in an amount of 0–80 wt. %.

As the resoiling preventives, there are used polyethylene glycol, polyacrylates, polyacrylic acid copolymers such as acrylic acid-maleic acid copolymers, polyvinyl alcohol, polyvinyl pyrrolidone, carboxymethyl cellulose and the like. Part of the resoiling preventives may also be used as divalent metal ion sequestrants. The resoiling preventives are incorporated in an amount of 0–10 wt. %, preferably 1–5 wt. %.

As the enzymes, there may be used cellulase, α-amylase, pululanase, lipase, hemicellulase, β-glycosidase, glucose oxidase, cholesterol oxidase, protease and the like.

Examples of the scavengers for available chlorine in tap water include ammonium sulfate, urea, guanidine hydrochloride, guanidine carbonate, guanidine sulfamate, thiourea dioxide, monoethanolamine, diethanolamine, triethanolamine, amino acids typified by glycine and sodium glutamate, and proteins such as bovine serum albumin and casein, and besides hydrolyzates of proteins, meat extracts and fish meat extracts. Examples of the reducing agents include alkali metal salts and alkaline earth metal salts such as the thiosulfates, sulfites and dithionites of these metals, and Rongalit C. The sulfites are particularly preferred and serve to stabilize enzymes in washing liquid.

Examples of the bleaching agent include percarbonates, perborates, zinc or aluminum sulfonated phthalocyanine, and hydrogen peroxide. When they are used in a bleaching detergent, sodium peroxide is particularly effective. Its amount to be incorporated is preferably 1–95 wt. %, more preferably 5–95 wt. %, most preferably 20–95 wt. %.

Examples of the fluorescent dyes include fluorescent dyes used generally in detergents. In the case of a liquid detergent, a solubilizing agent, for example, a lower alcohol such as ethanol, a benzenesulfonate, a lower alkyl-benzenesulfonate such as p-toluenesulfonate, glycerol, or a polyol such as propylene glycol may be incorporated.

The detergent compositions according to the present invention can be prepared by using the compound (1) according to the present invention in combination with the above-described known components in accordance with a method known per se in the art. The form of the detergents may be selected according to the intended application, and the detergents may be prepared in the form of, for example, liquid, powder or granules.

EXAMPLES

The present invention will hereinafter be described in more detail by the following examples. However, the present invention is not limited to and by these examples.

Referential Example 1

A reactor was charged with 50 g (0.67 mole) of glycine, 70 g of water and 27 g (0.67 mole) of sodium hydroxide, and the contents were cooled down to 5° C. Thereafter, 124 g (1.34 moles) of epichlorohydrin were added dropwise over 1.5 hours, and the resultant mixture was heated up to room temperature. After the mixture was stirred for 6 hours, insoluble matter deposited was separated by filtration and dried to obtain 106 g (isolation yield: 56%) of sodium N,N-bis(3-chloro-2-hydroxypropyl)-glycine as white powder.

The 1H-NMR data of this product will be shown below.

$^1$-NMR (D$_2$O): δ(ppm) D$_2$O standard 4.75 2.58–2.85 (complicated multiplet,4H,a), 3.27 (singlet,2H,b), 3.44–3.76 (complicated multiplet,4H,c), 3.88–4.09 (complicated multiplet,2H,d).

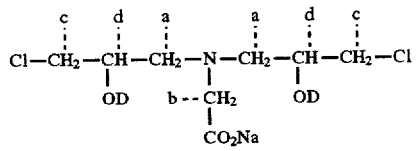

Example 1

A reactor was charged with 40 g (0.14 mole) of sodium N,N-bis(3-chloro-2-hydroxypropyl)glycine obtained in the same manner as in Referential Example 1, 100 g of methanol and 181 g (1.4 moles) of octylamine, and the contents were heated to 90° C. After stirring the mixture for 10 hours, an aqueous solution of 11 g of sodium hydroxide was added. Thereafter, water and methanol were distilled off under reduced pressure, and unreacted octylamine was further distilled off at 100° C. and 0.5 mmHg. To the residue were added 700 ml of hexane and 700 ml of water, and the resultant xylene layer was taken out and concentrated, thereby obtaining 47 g (isolation yield: 79%) of 13-carboxymethyl-11,15-dihydroxy-9,13,17-triazapentacosane.

The $^1$H-NMR data of this product will be shown below.

$^1$H-NMR: δ(ppm) CDCl$_3$ 0.88 (triplet,6H,a), 1.25 (broad singlet,20H,b), 1.45 (broad singlet,4H,c), 2.31–2.70 (complicated multiplet,12H,d), 3.20 (singlet,2H,e), 3.75 (broad singlet,2H,f).

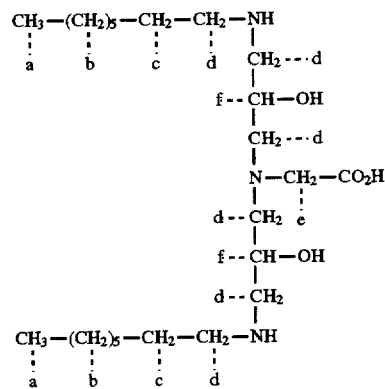

Example 2

A reactor was charged with 20 g (0.07 mole) of sodium N,N-bis(3-chloro-2-hydroxypropyl)glycine obtained in the same manner as in Referential Example 1 and 100 g of water, and the contents were kept at 50° C., to which 35 ml of a 4N aqueous solution of sodium hydroxide were added. After the mixture was stirred for 30 minutes, the solvent was distilled off under reduced pressure, and 100 ml of ethanol were added to the residue to separate insoluble matter by filtration. Thereafter, ethanol was distilled off under reduced pressure, thereby obtaining 11 g (isolation yield: 84%) of N,N-bis(2,3-epoxypropyl)glycine.

The $^1$H-NMR data of this product will be shown below.

$^1$H-NMR (D$_2$O): δ(ppm) D$_2$O standard 4.75 2.45–2.86 (complicated multiplet,8H,a), 3.11 (complicated multiplet, 2H,b), 3.29 (singlet,2H,c).

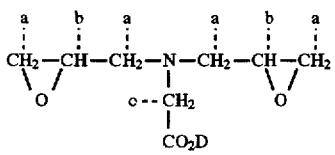

Example 3

A reactor was charged with 26.5 g (0.6 mole) of 13-carboxymethyl-11,15-dihydroxy-9,13,17-triazapentacosane obtained in the same manner as in Example 1 and 40 g of ethanol, and the contents were heated to 50° C., to which a solution with 40 g (0.34 mole) of sodium monochloroacetate dissolved in 80 g of water and 20 g of ethanol was added. While keeping the pH of the mixture at 8–10 with an aqueous solution of sodium hydroxide, a reaction was conducted for 30 hours. After completion of the reaction, ethanol was distilled off under reduced pressure, and the residue was dissolved in 500 ml of water. An inorganic salt formed and unreacted sodium chloroacetate were removed from the solution by electrodialysis, and the thus-treated solution was lyophilized, thereby obtaining 22 g (isolation yield: 65%) of 11,15-dihydroxy-9,13,17-triaza-9,13,17-tricarboxymethylpentacosane as white powder.

The $^1$H-NMR data of this product will be shown below.

$^1$H-NMR: δ(ppm) D$_2$O 0.86 (triplet,6H,a), 1.22 (broad singlet,20H,b), 1.41 (broad singlet,4H,c), 2.40–2.83 (complicated multiplet,12H,d) 3.20 (broad singlet,6H,e), 3.72 (broad singlet,2H,f).

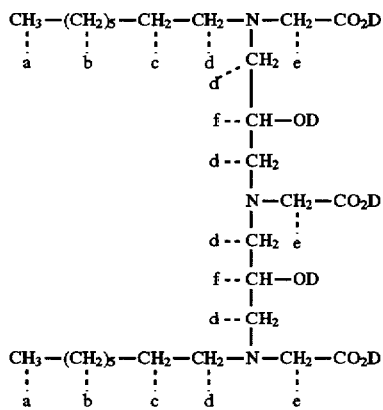

Example 4

A reactor was charged with 30 g (0.24 mole) of taurine, 30 g of water and 9.65 g of sodium hydroxide, and the contents were cooled to 10° C. To the mixture, 44.7 g (0.48 mole) of epichlorohydrin were added dropwise over 30, and the resultant mixture was heated up to room temperature. After a reaction was conducted at room temperature for 5 hours, 347 g (2.7 moles) of octylamine and 100 g of methanol were added, and the resulting mixture was heated to 50° C. After a reaction was conducted at 50° C. for 16 hours, water and methanol were distilled off under reduced pressure, and unreacted octylamine was then distilled off at 100° C. and 0.5 mmHg. To the residue were added 800 ml of chloroform and 800 ml of a 5% aqueous solution of sodium hydroxide to conduct extraction and washing with water. The resultant chloroform layer was taken out, and the solvent was distilled out of the chloroform layer, thereby obtaining 94 g (isolation yield: 79%) of 11,15-dihydroxy-13-sulfoethyl-9,13,17-triazapentacosane.

The $^1$H-NMR data of this product will be shown below.

$^1$H-NMR: δ(ppm) CDCl$_3$ 0.84 (triplet,6H,a), 1.26 (broad singlet,20H,b), 1.44 (broad singlet,4H,c), 2.15–2.50 (complicated multiplet,2H,d), 2.61–2.87 (complicated multiplet,14H,e), 3.44–3.63 (complicated multiplet, 2H, f).

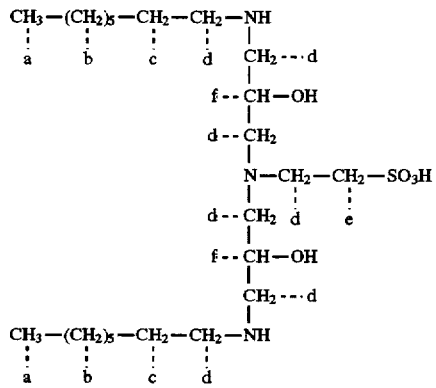

Example 5

A reactor was charged with 20 g (0.04 mole) of 11,15-dihydroxy-13-sulfoethyl-9,13,17-triazapentacosane obtained in the same manner as in Example 4 and 35 g of ethanol, and the contents were heated to 60° C., to which a solution with 29 g (0.15 mole) of sodium 3-chloro-2-hydroxypropane-sulfonate dissolved in 35 g of water was added dropwise over 1.5 hours. During the drop addition, the pH of the reaction mixture was kept at 8–10 with aqueous sodium hydroxide. After the reaction mixture was stirred at 60° C. for 33 hours, ethanol was distilled off under reduced pressure. The residue was then dissolved again in 500 ml of water, and the solution was desalted by electrodialysis and lyophilized, thereby obtaining 24 g (isolation yield: 78%) of 2,6,10,14-tetrahydroxy-4,12-dioctyl-8-sulfoethyl-4,8,12-triazapentadecane-1,15-disulfonic acid as white powder.

The $^1$H-NMR data of this product will be shown below.

$^1$H-NMR: δ(ppm) D$_2$O 0.81 (triplet,6H,a), 1.25 (broad singlet,20H,b), 1.47 (broad singlet,4H,c), 2.11–2.56 (complicated multiplet,6H,f), 2.73–2.94 (complicated multiplet,18H,d), 3.70–3.85 (complicated multiplet,2H,e), 3.98 (broad singlet,2H,g).

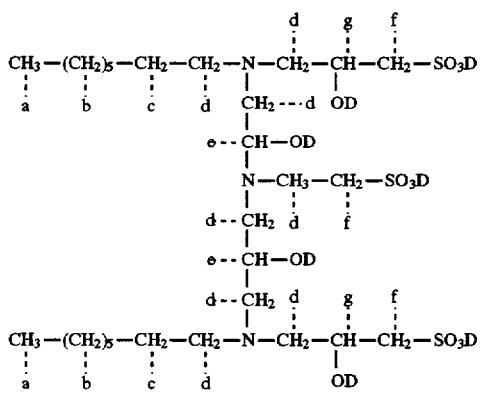

Example 6

A reactor was charged with 27 g (0.05 mole) of 11,15-dihydroxy-13-sulfoethyl-9,13,17-triazapentacosane and 100 g of xylene, to which 12 g (0.12 mole) of succinic anhydride were then added with stirring to conduct a reaction at 50° C. for 6 hours. After xylene was distilled off under reduced pressure, 300 ml of water were added, and 10% sodium hydroxide was further added to keep the pH of the reaction mixture at 7. Thereafter, the reaction mixture was subjected to electrodialysis and lyophilized, thereby obtaining 28 g (isolation yield: 76%) of 6,10-dihydroxy-4,12-dioctyl-3,13-dioxo-8-sulfoethyl-4,8,12-triaza-1,15-pentadecanedicarboxylic acid as white crystals.

The $^1$H-NMR data of this product will be shown below.

$^1$H-NMR: δ(ppm) D$_2$O 0.85 (triplet,6H,a), 1.28 (broad singlet,20H,b), 1.46 (broad singlet,4H,c), 2.15–2.55 (complicated multiplet,2H, g), 2.61–2.90 (complicated multiplet,14H,f), 3.20–3.58 (complicated multiplet,8H,d), 3.75–3.84 (complicated multiplet,2H,e).

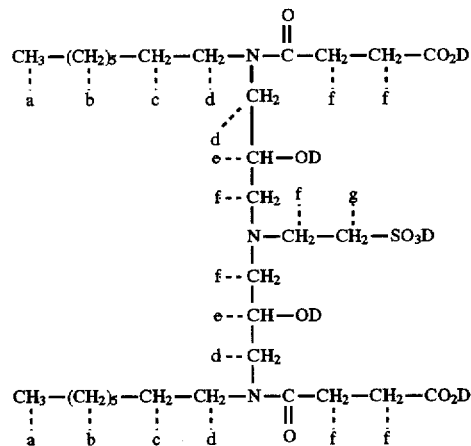

Further, the above compound was dispersed in water, and aqueous sodium hydroxide in an amount equivalent to this compound was added to the dispersion. The resultant product was lyophilized to obtain its corresponding sodium salt.

Example 7

A reactor was charged with 20 g (0.04 mole) of 11,15-dihydroxy-13-sulfoethyl-9,13,17-triazapentacosane and 100 g of xylene, to which 10 g (0.1 mole) of maleic anhydride were then added with stirring to conduct a reaction at 50° C. for 6 hours. After xylene was distilled off under reduced pressure, 300 ml of water were added, and 10% sodium hydroxide was further added to keep the pH of the reaction mixture at 7. Thereafter, the reaction mixture was subjected to electrodialysis and lyophilized, thereby obtaining 22 g (isolation yield: 80%) of 6,10-dihydroxy-4,12-dioctyl-3,13-dioxo-8-sulfoethyl-4,8,12-triaza-1,14-pentadecadiene-1,15-dicarboxylic acid as white powder.

The $^1$H-NMR data of this product will be shown below.

$^1$H-NMR: δ(ppm) D$_2$O 0.88 (triplet,6H,a), 1.25 (broad singlet,20H,b), 1.44 (broad singlet,4H,c), 2.15–2.55 (complicated multiplet,2H,g), 2.60–2.85 (complicated multiplet,6H,f), 3.23–3.57 (complicated multiplet,8H,d), 3.77–3.85 (complicated multiplet,2H,e), 6.11–6.65 (complicated multiplet,4H,h).

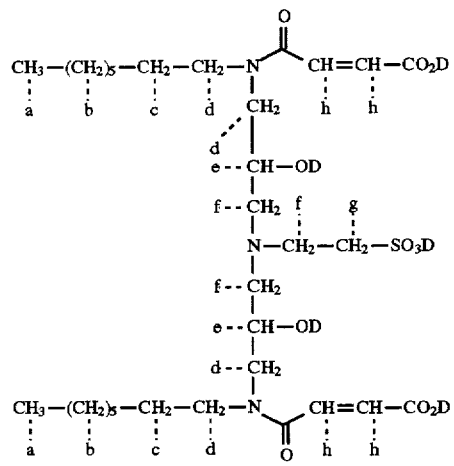

Further, the above compound was dispersed in water, and aqueous sodium hydroxide in an amount equivalent to this compound was added to the dispersion. The resultant product was lyophilized to obtain its corresponding sodium salt.

Example 8

A reactor was charged with 20 g (0.029 mole) of 6,10-dihydroxy-4,12 -dioctyl-3,13-dioxo-8-sulfoethyl-4,8,12-triaza-1,14-pentadecadiene-1,15-dicarboxylic acid obtained in Example 7 and 70 ml of an aqueous solution of 8 g (0.064 mole) of sodium sulfite, and the reaction mixture was stirred at 60° C. for 3 hours while keeping its pH at 5–6. After completion of the reaction, the pH of the liquid reaction mixture was adjusted to 7 with 1N aqueous sodium hydroxide, and an excess amount of sodium sulfite was removed by electrodialysis. Thereafter, the thus-treated mixture was lyophilized, thereby obtaining 21 g (isolation yield: 86%) of sodium 1,15-dicarboxy-6,10-dihydroxy-4,12-dioctyl-3,13-dioxo-8-sulfoethyl-4,8,12-triazapentadecane-1,15-disulfonate as white powder.

The $^1$H-NMR data of this product will be shown below.

$^1$H-NMR: δ(ppm) D$_2$O 0.88 (triplet,6H,a), 1.27 (broad singlet,20H,b), 1.48 (broad singlet,4H,c), 2.10–2.49 (complicated multiplet,2H,g), 2.55–2.92 (complicated multiplet,10H,f), 3.22–3.58 (complicated multiplet,10H,d), 3.79–3.88 (complicated multiplet,2H,e).

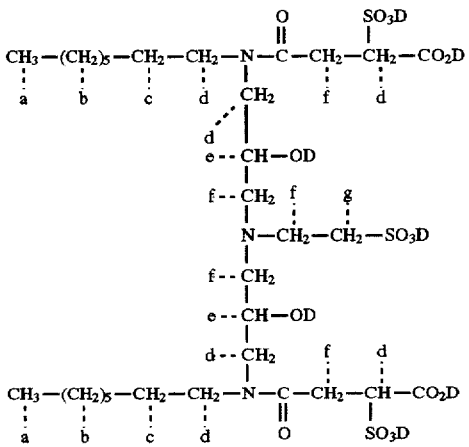

Further, the above compound was dispersed in water, and aqueous sodium hydroxide in an amount equivalent to this compound was added to the dispersion. The resultant product was lyophilized to obtain its corresponding sodium salt.

Example 9

A reactor was charged with 10 g (0.02 mole) of 11,15-dihydroxy-13-sulfoethyl-9,13,17-triazapentacosane, 50 ml of toluene and 5.1 ml (0.05 mole) of ethyl glycolate, and the contents were heated to 100° C. and continuously stirred for 7.5 hours while purging ethanol formed with a nitrogen stream. After completion of a reaction, the solvent was distilled off under reduced pressure, and the residue was purified by column chromatography (on 200 g of silica gel, developing solvent: chloroform/methanol=100/1→20/1), thereby obtaining 10.6 g (isolation yield: 91%) of 3,11-dioctyl-2,12-dioxo-7-sulfoethyl-3,7,11-triaza-1, 5,9,13-tridecanetetraol.

The $^1$H-NMR data of this product will be shown below.

H-NMR: δ(ppm) $D_2O$ 0.85 (triplet,6H,a), 1.27 (broad singlet,20H,b), 1.43 (broad singlet,4H,c), 2.11–2.50 (complicated multiplet,2H,h), 2.63–2.88 (complicated multiplet,6H,f), 3.20–3.55 (complicated multiplet,8H,d), 3.88–3.91 (complicated multiplet,2H,e), 4.15 (broad singlet, 4H,g).

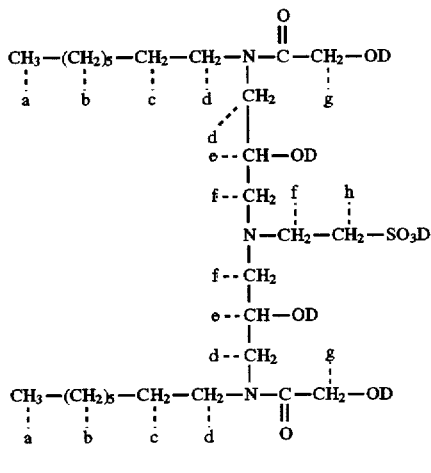

Example 10

A reactor was charged with 10 g (0.016 mole) of 3,11-dioctyl-2,12-dioxo-7-sulfoethyl-3,7,11-triaza-1, 5,9,13-tridecanetetraol obtained in Example 9 and 100 ml of dichloromethane, to which 2.2 ml (0.032 mole) of chlorosulfonic acid was added dropwise in a nitrogen stream while chilling with ice water. Thereafter, the temperature of the resulting mixture was gradually raised to room temperature, and hydrochloric acid and dichloromethane generated were purged with a nitrogen stream. Water was added to the residue to dissolve the residue therein, and the pH of the solution was adjusted to 7 with 1N aqueous sodium hydroxide. The thus-treated solution was desalted by electrodialysis and then lyophilized, thereby obtaining 9.2 g (isolation yield: 75%) of disodium 5,9-dihydroxy-7-sulfoethyl-2,12-dioxo-3,11-dioctyl-3,7,11-triaza-1,12-tridecanedisulfate.

IR (KBr briquette method, cm$^{-1}$): 1388, 1184 ($v_{S=O}$), 1660($v_{C=O}$).

Formulation Example 1

A shampoo having the following composition was prepared using the compound according to the present invention.

| (Composition) | (wt. %) |
| --- | --- |
| Compound of Example 3 | 15.0 |
| Lauroyldiethanolamide | 3.0 |
| Lauryldimethylamine oxide | 0.5 |
| Hydroxyethyl cellulose (product of Daicel Chemical Industries, Ltd.) | 0.1 |
| Sodium benzoate | 0.3 |
| Coloring matter | q.s. |
| Perfume base | q.s. |
| Citric acid | q.s. |
| Water | Balance |
| Total | 100.0 |

Formulation Example 2

Shampoos were prepared in the same manner as in Formulation Example 1 except that the compound of Example 5, 6, 7, 8 or 10 was used in place of the compound of Example 3.

All the shampoos obtained in Formulation Examples 1 and 2 were excellent in foamability and detergency, and also good in feeling upon both shampooing and rinsing.

Formulation Example 3

A body shampoo having the following composition was prepared using the compound according to the present invention.

| (Composition) | (wt. %) |
| --- | --- |
| Compound of Example 3 | 17.0 |
| Polyoxyethylene (EO 3) laurylglucoside | 5.0 |
| Lauryldimethylamine oxide | 3.0 |
| Glycerol | 4.0 |
| Sucrose fatty acid ester | 1.0 |
| Methylparaben | 0.3 |
| Coloring matter | q.s. |
| Perfume base | q.s. |
| Citric acid | q.s. |
| Water | Balance |
| Total | 100.0 |

Formulation Example 4

Body shampoos were prepared in the same manner as in Formulation Example 3 except that the compounds of Example 5, 6, 7, 8 or 10 was used in place of the compound of Example 3.

All the body shampoos obtained in Formulation Examples 3 and 4 were excellent in foamability and detergency, and also good in the feeling after washing because they gave a moisturized feeling.

Formulation Example 5

A powdery laundry detergent composition having the following composition was prepared. This detergent composition was excellent in detergency at a low temperature (5° C.), and its detergency was not impaired even when water high in hardness (4°–8° DH) was used.

| (Composition) | (wt. %) |
|---|---|
| Compound of Example 3, 5, 6, 8 or 10 | 5.0 |
| Polyoxyethylene (EO 4-18) $C_8$–$C_{22}$-alkyl ether | 3.0 |
| Na $C_{12}$-alkylbenzenesulfonate | 20.0 |
| Na $C_{12}$–$C_{14}$-alkylsulfate | 5.0 |
| Na salt of $C_{12}$–$C_{18}$ fatty acid | 6.0 |
| Zeolite (4A type) | 30.0 |
| Sodium carbonate | 20.0 |
| Enzyme (protease, cellulase) | 2.0 |
| Polymer (acrylic acid-maleic acid copolymer, Mw = 50,000) | 3.0 |
| Fluorescent dye (DM type, Tinopal CBS mixed system) | 0.5 |
| Perfume base | 0.2 |
| Water | Balance |
| Total | 100.0 |

Formulation Example 6

A powdery laundry detergent having the following composition and composed principally of a nonionic surfactant was prepared. According to this detergent, the disadvantages that foaming upon washing is little and rinsability is poor, which are problems involved in the conventional detergents composed principally of a nonionic surfactant, were improved.

| (Composition) | (wt. %) |
|---|---|
| Compound of Example 3, 5, 6, 8 or 10 | 5.0 |
| Polyoxyethylene (EO 4-18) $C_6$–$C_{22}$-alkyl ether | 22.0 |
| Na salt of $C_{12}$–$C_{18}$ fatty acid | 1.0 |
| Zeolite (4A type) | 30.0 |
| Sodium carbonate | 25.0 |
| Amorphous aluminosilicate ($Na_2O.Al_2O_3.3SiO_2$) | 10.0 |
| Enzyme (protease, cellulase) | 2.0 |
| Polymer (acrylic acid-maleic acid copolymer, Mw = 100,000) | 3.0 |
| Fluorescent dye (DM type, Tinopal CBS mixed system) | 0.5 |
| Perfume base | 0.2 |
| Water | Balance |
| Total | 100.0 |

Test Example 1

A dishwashing detergent having the following composition was prepared to evaluate it in foaming power, detergency, irritativeness to the skin and a feeling upon use (feeling of touch to the hands).

| (Composition) | (wt. %) |
|---|---|
| Compound of Example 3, 5 or 8 | 5.0 |
| Sodium polyoxyethylene (average number of moles added: 3) lauryl ether sulfate | 12.0 |
| Lauryldimethylamine oxide | 3.0 |
| Coconut oil fatty acid monoethanolamide | 5.0 |
| Ethanol | 2.5 |
| Sodium m-xylenesulfonate | 2.0 |
| Sodium benzoate | 1.0 |
| Coloring matter | q.s. |
| Perfume base | q.s. |
| Water | Balance |
| Total | 100.0 |

<Testing method>

Beef tallow added with 0.1 wt. % of Sudan III (a red coloring matter) as an indicator was applied in an amount of 2.5 g to a porcelain dish (diameter: 25 cm). The thus-smeared dish was rubbed and washed at 40° C. by means of a sponge with 3 g of the detergent sample and 27 g of water (hardness: 3.5° DH) soaked therein. The above-described test was conducted on ten panelists to evaluate the detergent sample in the detergency, feeling upon use, etc.

<Results>

As a result, the dishwashing detergent in which the compound according to the present invention was incorporated was good in foaming power, high in detergency and low in irritativeness to the hands and gave users a pleasant feeling upon use.

INDUSTRIAL APPLICABILITY

The amine compounds (1), or salts or quaternized products of these compounds, which are novel compounds according to the present invention, are excellent in foamability and low in irritativeness to the skin and the like, and can give a pleasant feeling to the user's skin, hair and the like. Therefore, the compounds according to the present invention are useful as bases for hair and skin cosmetic compositions, detergents, emulsifying agents, wetting agents, conditioning agents, modifiers and the like.

We claim:

1. An amine compound represented by the following general formula (1):

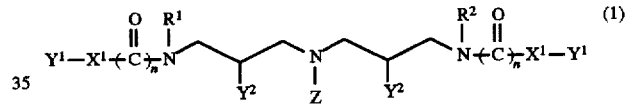

wherein $R^1$ and $R^2$ are the same or different from each other and represent individually a linear or branched alkyl or alkenyl group which may be substituted by a hydroxyl group and has 1–24 carbon atoms, $X^1$ represents an alkylene or alkenylene group which may be substituted by at least one hydroxyl, sulfonic or carboxyl group and has 1–6 carbon atoms, $Y^1$ represents a carboxyl or sulfonic group, or a sulfuric acid residue, $Y^2$ represents a hydroxyl group, a sulfuric acid residue or a group —OCO—$X^1$—COOH, Z represents a sulfoalkyl group or a group obtained by removing an amino group from an amino acid or a salt thereof, and n represents a number of 0 or 1, or a salt or quaternized product thereof.

2. The compound according to claim 1, wherein in the general formula (1), $R^1$ and $R^2$ are individually a linear or branched alkyl group having 6–24 carbon atoms, $Y^1$ is a carboxyl or sulfonic group, $Y^2$ is a hydroxyl group, and Z is a sulfoalkyl group or a group obtained by removing an amino group from a protein-constituting amino acid or β-alanine, or a salt thereof.

3. The compound according to claim 1, wherein in the general formula (1), $R^1$ and $R^2$ are individually a linear or branched alkyl group having 6–24 carbon atoms, $X^1$ is an alkylene or alkenylene group which may be substituted by at least one hydroxyl group and has 1–6 carbon atoms, $Y^1$ is a sulfuric acid residue, and Z is a sulfoalkyl group or a group obtained by removing an amino group from a protein-constituting amino acid or β-alanine, or a salt thereof.

4. An aminoalcohol compound represented by the following general formula (2):

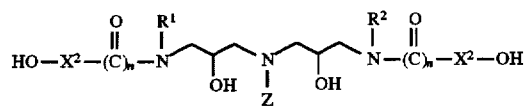

(2)

wherein $R^1$ and $R^2$ are the same or different from each other and represent individually a linear or branched alkyl or alkenyl group which may be substituted by a hydroxyl group and has 1-24 carbon atoms, $X^2$ represents an alkylene or alkenylene group which may be substituted by at least one hydroxyl group and has 1-6 carbon atoms, Z represents a sulfoalkyl group or a group obtained by removing an amino group from an amino acid or a salt thereof, and n represents a number of 0 or 1.

5. The compound according to claim 4, wherein in the general formula (2), $R^1$ and $R^2$ are individually a linear or branched alkyl group having 6-24 carbon atoms, and Z is a sulfoalkyl group or a group obtained by removing an amino group from a protein-constituting amino acid or β-alanine, or a salt thereof.

6. A detergent composition comprising the amine compound, or the salt or quaternized product thereof according to any one of claims 1.

* * * * *

UNITED STATES PATENT AND TRADEMARK OFFICE
CERTIFICATE OF CORRECTION

PATENT NO. : 5,723,655
DATED : March 3, 1998
INVENTOR(S) : Mitsuru Uno et al.

It is certified that error appears in the above-identified patent and that said Letters Patent is hereby corrected as shown below:

<u>Title page,</u>
Item [86], §371 Date and §102 (e) Date should be -- Jan. 7, 1997 --

Signed and Sealed this

Second Day of July, 2002

Attest:

Attesting Officer

JAMES E. ROGAN
Director of the United States Patent and Trademark Office